United States Patent
Meshram et al.

(10) Patent No.: US 6,777,553 B1
(45) Date of Patent: Aug. 17, 2004

(54) PROCESS FOR SYNTHESIS OF BIS-(SUBSTITUTED-4-QUINOLYL) DISULPHIDES

(75) Inventors: Harshadas Mitaram Meshram, Andhra Pradesh (IN); Premalatha Kokku, Andhra Pradesh (IN); Venkata Madhavi Ayyagiri, Andhra Pradesh (IN); Eshwaraiah Begari, Andhra Pradesh (IN); Jhillu Singh Yadav, Andhra Pradesh (IN)

(73) Assignee: Council of Scientific and Industrial Research

( * ) Notice: Subject to any disclaimer, the term of this patent is extended or adjusted under 35 U.S.C. 154(b) by 0 days.

(21) Appl. No.: 10/395,854

(22) Filed: Mar. 25, 2003

(51) Int. Cl.[7] .................. C07D 215/36; A61K 31/47
(52) U.S. Cl. .................. 546/153; 546/153; 514/312
(58) Field of Search .................. 546/153; 514/312

(56) References Cited

PUBLICATIONS

CAPLUS listing of Monti, Lydia et al., "Some derivatives of thioquinoline, III", Gazzetta Chimica Italiana (1959), Univ. Siena, Italy, vol. 89, pp. 1084–1091, Doc. No. 55:2680.*
CAPLUS listing of Konishi et al, WO 96/23774 (1996), all pages.*

* cited by examiner

*Primary Examiner*—Ceila Chang
*Assistant Examiner*—Janet L Coppins
(74) *Attorney, Agent, or Firm*—Nixon & Vanderhye P.C.

(57) ABSTRACT

The present invention relates to a process for the synthesis of bis-(substituted-4-quinolyl) disulphides.

9 Claims, No Drawings

PROCESS FOR SYNTHESIS OF BIS-(SUBSTITUTED-4-QUINOLYL) DISULPHIDES

FIELD OF THE INVENTION

The present invention relates to a process for the synthesis of bis-(substituted-4-quinolyl) disulphides.

BACKGROUND OF THE INVENTION

Substituted bis-quinolyl disulphides are known for antimalarial activity and some of them are used as analytical reagents. In recent studies it is stated that these compounds have selective and efficacious antibacterial activity on bacteria belonging to the Helicobacter and are also useful for the treatment or prevention of recurrence of peptic ulcer and chronic stomach inflammation accompanied by H bacteria infection.

Reference is made to Japan Patent, JP Appl. 95/14,233, 31 Jan. 1995 PCT Int.Appl. WO96 23,774 (Cl. C07D215/36),8 Aug. 1996, CA:125,247631h; (japan) wherein quinoline 4(1H)-thione was oxidized to disulphide using potassium ferricyanide. This process has draback of preparing thione and using expensive potassium ferricyanide.

Reference is made to *Latv. PSR Zinat. Acad. Vestis, Kim. Ser.* 1979,(9),181(Russ), CA:91,39289c and *Latv. PSR Zinat. Acad. Vestis, Kim. Ser.* 1979,(3),282(Russ),CA:91, 193129j wherein chlorosulphonyl derivative of quinoline is converted to thiol by reduction which on oxidation gave disulphide. This process has draback of using hazardous and corrosive chlorosulphonic acid.

Reference is further made to *Latv. PSR Zinat. Acad. Vestis, Kim. Ser.* 1980,(4)489 (Russ),CA: 94,15526r which involve the diazotization of amino quinoline followed by reaction with thiourea gives thiol. The oxidation of thiol gives disulphide. In this process, crucial diazotization reaction requires great precautions.

Reference is also made to *Pharmazine* 1978,33(9),572, CA: 89, 215199v which involves the reaction of chloroquinoline with thioacetamide or thiourea to form thiol derivatives which on further oxidation gives disulphide. This particular process has drawback of using higher temperature.

All the earlier processes involve the use of corrosive and hazardous chlorosulphonic acid, crucial diazotization, and higher reaction temperature. Moreover, the isolation of thiol from aqueous medium is tedious. Although practiceable in laboratory, all these methods have little feasibility on commercial scale in term of steps involved, cost, handling of hazardous reagents and waste effluents. Therefore existing methods for the preparation of bis-quinolyl disulphides have following disadvantages.

1. Handling of hazardous and corrosive chlorosulphonic acid is difficult.
2. Diazotization reaction require great precaution.
3. Isolation of thiol from aqueous medium is troublesome.
4. Involve additional oxidation step
5. Require higher reaction temperature.
6. Number of steps involved are more.

OBJECTS OF THE INVENTION

The main object of the present invention is to provide a process for the preparation of bis(substituted-4-quinolyl) disulphide using substituted-4-haloquinolines and the sodium, potassium or ammonium salts of dithiocarbamic acid which avoids the drawbacks as detailed above.

Another object of the present invention is to develop a process for bis(substituted-4-quinolyl) disulphides without the use of hazardous chlorosulphonyl derivatives and additional oxidizing reagent.

Yet another object of the invention is to avoid the crucial diazotization and isolation of thiol from aqueous medium.

Yet another object of the invention is to use inexpensive, non-hazardous salt of dithiocarbamic acid which reduces the number of steps, minimize the waste effluent in large scale.

Yet another object of the invention is to provide a process for the preparation of bis(substituted-4-quinolyl) disulphide wherein the byproduct disubstituted thiourea is also useful as value added product, thereby improving the economy of the process.

It is yet another object of the invention to provide a process for the preparation of bis(substituted-4-quinolyl) disulphide which avoids the use of hazardous and corrosive chlorosulphonic acid, excessive and stringent precautions required for diazotization, difficulty in isolation of thiol from aqueous medium, avoids the additional oxidation step and avoids the requirement of higher reaction temperature.

SUMMARY OF THE INVENTION

The present process is useful for the one pot preparation of bis(substituted-4-quinolyl) disulphides using substituted-4-haloquinoline and sodium, potassium or ammonium salt of dithiocarbamic acid in aprotic solvent. Further aim of the process is to avoid the use of corrosive chlorosulphonyl chloride or expensive oxidizing reagents or isolation of unstable thiols. The important feature of the invention is that disulphides are prepared in one step which avoids the number of troublesome steps and use of hazardous corrosive chemicals. The yield of the disulphides is also high Accordingly, the present invention provides a one step process for the preparation of bis-(substituted-4-quinolyl) disulphide of the formula 1

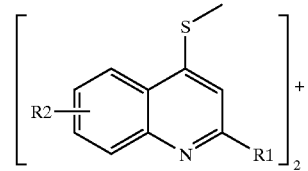

Formula 1 wherein R1 is selected from the group consisting of trifluoro, trichloro, cyano and substituted amide; R2 is selected from the group consisting of alkyl, alkoxy, halogen, alkylamino; comprising reacting substituted-4-haloquinoline and a salt of alkyl or aryl dithiocarbamic acid in an organic solvent to obtain said bis-(substituted-4-quinolyl) disulphide of the formula 1 and disubstituted thiourea of the formula 2

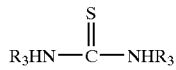

Formula 2

In one embodiment of the invention the halo in the substituted-4-haloquinoline is selected from the group consisting of iodo, bromo, chloro and fluoro.

In another embodiment of the invention, the substituents on quinoline at 2-position are selected from the group consisting of trifluoromethyl, trichloromethyl, cyano and substituted amide.

In yet another embodiment of the invention, the substituents on quinoline at the 5,6,7 or 8 position are selected from the group consisting of halogen, alkyl, alkoxy and alkylamino.

In a further embodiment of the invention, the salt of alkyl or aryl dithiocarbamic acid is selected from the group consisting of sodium, potassium and ammonium salts.

In another embodiment of the invention, the organic solvent is selected from group consisting of dimethylformamide, dimethylsulphoxide, mixture thereof and acetonitrile.

In a further embodiment of the invention, the reaction is carried out at a temperature in the range of 20° C. to 40° C.

In a further embodiment of the invention, the reaction is carried out for a time period in the range of 6 to 17 hrs.

In yet another embodiment of the invention, the yield of the bis-(substituted-4-quinolyl) disulphide of the formula 1 is in the range of 70 to 80%.

DETAILED DESCRIPTION OF THE INVENTION

The present process is useful for the one pot preparation of bis(substituted-4-quinolyl) disulphides using substituted-4-haloquinoline and sodium, potassium or ammonium salt of dithiocarbamic acid in aprotic solvent. Further aim of the process is to avoid the use of corrosive chlorosulphonyl chloride or expensive oxidizing reagents or isolation of unstable thiols. The important feature of the invention is that disulphides are prepared in one step which avoids the number of troublesome steps and use of hazardous, corrosive chemicals. The yield of the disulphides is also high Scheme 1 represent the preparation of bis(substituted-4-quinolyl) disulphide Scheme I

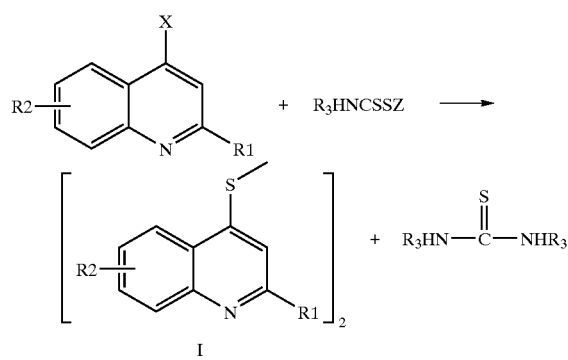

$R_1$ = trifluoro, trichloro, cyano, substituted amide
$R_2$ = alkyl, alkoxy, halogen, alkylamino
$R_3$ = ($C_1$–$C_4$)alkyl or aryl
Z = Na, K or $NH_4$ To overcome with the difficulties associated with earlier processes for the preparation of bis(substituted-4-quinolyl) disulphide, the inventors of present invention have disclosed the process for the preparation of bis-(substituted-4-quinolyl) disulphides using substituted 4-haloquinolines and the sodium, potassium and ammonim salt of alkyl or aryl dithiocarbamic acid in polar solvent. The disulphide formation occurs in one step, which was isolated by filtration or extraction.

EXAMPLE 1

Bis(2,8-trifluoromethyl quinolyl) disulphide

A mixture of (2,8-trifluoromethyl)-4-bromoquinoline (0.1 mol) and potassium salt of ethyl dithiocarbamic acid (0.15 mol) in dimethylformamide(300 ml) is stirred at 20° C. for 10 hours. It is poured in water and extracted with ether. After evaporation, the product is isolated using a mixture of hexane:ether(90:10). Yield 75%.

EXAMPLE 2

Bis(2,8-trifluoromethyl quinolyl) disulphide 2,8-Trifluoromethyl-4-iodoquinoline(0.1 mol) is dissolved in dimethylformamide (350 ml) and phenyl ammonium dithiocarbamate(0.15 mol) is added to it maintaining the temperature 15° C. Stirring continued at 25° C. for 9 hrs, diluted with water and extracted with ether. After evaporation of solvent, the residue is extracted with toluene. Removal of toluene gives disulphide in the yield of 80%.

EXAMPLE 3

Bis(2-trifluoromethyl-8methyl quinolyl) disulphide

To a solution of 2-trifluoromethyl-8-methyl-4-bromoquinoline (0.1 mol) in dimethyl sulphoxide (300 ml), is added sodium salt of propyl dithiocarbamic acid (0.15 mol) in portions. The stirring continued at 35° C. for 13 hrs and solvent removed under vacuum. The residue extracted with a mixture of toluene:hexane (60:40), the removal of solvent gives disulphide yield 76%.

EXAMPLE 4

Bis(2-trifluoromethyl-8-chlorol quinolyl) disulphide

A mixture of 2-trifluoromethyl-8-chlorol-4-bromoquinoline (0.1 mol) in acetonitrile (400 ml) and sodium salt of methyl dithiocarbamic acid(0.18 mol) is stirred at 32° C. for 17 hrs. It is poured in water and extracted with ether. Removal of solvent gives crude product from which pure compound is obtained by the extraction with ether (4×100 ml), yield 75%.

EXAMPLE 5

Bis(2-trichloromethyl-8-trifluoromethyl-4-quinolyl) disulphide

Phenyl ammonium dithiocarbamate(0.13 mol) is added in portions to a cold solution of 2-trichloromethyl-8-trifluoromethyl-4-bromoquuinoline (0.1 mol) in dimethylformamide (300 ml).Then the mixture stirred at room temperature for 11 hrs. The solvent removed under vacuum and residue poured in water. The product isolated after extraction and crystallization, yield 77%.

We claim:

1. A one step process for the preparation of bis-(substituted4-quinolyl) disulphide of the formula 1

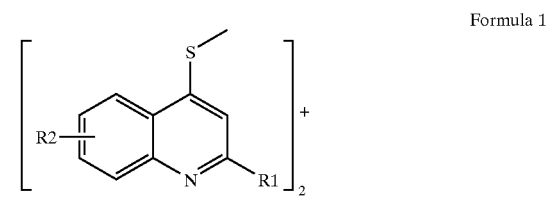

Formula 1 wherein R1 is selected from the group consisting of trifluoro, trichloro, cyano, or substituted amide; R2 is selected from the group consisting of alkyl, alkoxy, halogen, or alkylamino; comprising reacting a substituted 4-haloquinoline and a sodium, potassium, or ammonium salt of dithiocarbamic acid of the formula

wherein $R_3$ is selected from the group consisting of (C1–C$_4$) alkyl or aryl; and Z is selected from the group consisting of Na, K, or NH$_4$; in an organic solvent to obtain said bis-(substituted-4-quinolyl) disulphide of the formula 1 and a disubstituted thiourea of the formula 2

Formula 2

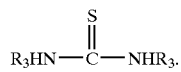

2. A process as claimed in claim 1 wherein the halo in the substituted-4-haloquinoline is selected from the group consisting of iodo, bromo, chloro and fluoro.

3. A process as claimed in claim 1 wherein the substituents on quinoline at 2-position are selected from the group consisting of trifluoromethyl, trichloromethyl, cyano and, substituted amide.

4. A process as claimed in claim 1 wherein the substituents on quinoline at the 5,6,7 or 8 position are selected from the group consisting of halogen, alkyl, alkoxy and alkylamino.

5. A process as claimed in claim 1 wherein the salt of alkyl or aryl dithiocarbamic acid is selected from the group consisting of sodium, potassium and ammonium salts.

6. A process as claimed in claim 1 wherein the organic solvent is selected from the group consisting of dimethylformamide, dimethylsulphoxide, a mixture thereof and acetonitrile.

7. A process as claimed in claim 1 wherein the reaction is carried out at a temperature in the range of 20° C. to 40° C.

8. A process as claimed in claim 1 wherein the reaction is carried out for a time period in the range of 6 to 17 hrs.

9. A process as claimed in claim 1 wherein the yield of the product bis-(substituted-4-quinolyl) disulphide of the formula 1 is in the range of 70 to 80%.

\* \* \* \* \*